(12) United States Patent
Tulkki et al.

(10) Patent No.: US 7,645,233 B2
(45) Date of Patent: Jan. 12, 2010

(54) POWERING A GUIDE WIRE MOUNTED SENSOR FOR INTRA-VASCULAR MEASUREMENTS OF PHYSIOLOGICAL VARIABLES BY MEANS OF INDUCTIVE COUPLING

(75) Inventors: Sauli Tulkki, Phuket (TH); Lars Tenerz, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 0 days.

(21) Appl. No.: 11/570,096

(22) PCT Filed: Jun. 7, 2005

(86) PCT No.: PCT/SE2005/000860

§ 371 (c)(1), (2), (4) Date: Dec. 6, 2006

(87) PCT Pub. No.: WO2005/120336

PCT Pub. Date: Dec. 22, 2005

(65) Prior Publication Data

US 2007/0255144 A1    Nov. 1, 2007

Related U.S. Application Data

(60) Provisional application No. 60/605,170, filed on Aug. 30, 2004, provisional application No. 60/577,197, filed on Jun. 7, 2004.

(51) Int. Cl.
*A61B 5/00* (2006.01)

(52) U.S. Cl. ............... 600/300; 600/481; 600/485; 600/345; 600/347; 600/549; 600/309

(58) Field of Classification Search ............ 600/481
See application file for complete search history.

(56) References Cited

U.S. PATENT DOCUMENTS 5,484,404 A * 1/1996 Schulman et al. ............ 604/66

(Continued)

*Primary Examiner*—Robert L Nasser
(74) *Attorney, Agent, or Firm*—Foley & Lardner LLP (57) ABSTRACT

The present invention relates to a sensor assembly arranged to be disposed in a body for measuring a physiological variable. A basic idea of the present invention is to provide a sensor and guide wire assembly which communicates with an external unit by an inductive coupling between a first coil provided in the sensor assembly and a second, external coil which is disposed in or connected to the external unit. The external unit is preferably the same unit that is used to numerically or graphically display the physiological variables that are measured with the sensor and guide wire assembly. With the terminology introduced above, it should here be clear that both the signal transfer from the sensor as well as the energy feeding from the external unit to the sensor may be accomplished through the inductive coupling between the first and second coils.

8 Claims, 8 Drawing Sheets

U.S. PATENT DOCUMENTS

| | | |
|---|---|---|
| RE35,648 E | 11/1997 | Tenerz et al. |
| 5,967,986 A | 10/1999 | Cimochowski et al. |
| 6,231,516 B1 * | 5/2001 | Keilman et al. ............. 600/485 |
| 6,264,611 B1 * | 7/2001 | Ishikawa et al. ............ 600/486 |
| 6,343,514 B1 | 2/2002 | Smith |
| 6,409,677 B1 * | 6/2002 | Tulkki ........................ 600/561 |
| 6,447,448 B1 * | 9/2002 | Ishikawa et al. ............ 600/300 |
| 6,565,514 B2 | 5/2003 | Svanerudh et al. |
| 6,615,067 B2 | 9/2003 | Hoek et al. |
| 6,692,446 B2 * | 2/2004 | Hoek ........................ 600/585 |
| 7,160,255 B2 * | 1/2007 | Saadat ....................... 600/549 |
| 2002/0138009 A1 | 9/2002 | Brockway et al. |
| 2005/0000294 A1 * | 1/2005 | Tenerz et al. .................. 73/727 |

* cited by examiner

POWERING A GUIDE WIRE MOUNTED SENSOR FOR INTRA-VASCULAR MEASUREMENTS OF PHYSIOLOGICAL VARIABLES BY MEANS OF INDUCTIVE COUPLING

TECHNICAL FIELD OF THE INVENTION

The present invention is related to a guide wire mounted sensor for intra-vascular measurements of physiological variables, e.g. pressure or temperature, inside a human or animal body, and to the way of displaying these measured physiological variables on a display unit, and in particular to the communication between the sensor and the display unit.

BACKGROUND OF THE INVENTION

Sensor and guide wire assemblies in which a sensor is mounted at the distal end of a guide wire are known. In U.S. Pat. Re. 35,648, which is assigned to the present assignee, an example of such a sensor and guide wire assembly is disclosed, where a sensor guide comprises a sensor element, an external electronic unit, several signal transmitting cables connecting the sensor element to the external electronic unit, a flexible tube having the cables and the sensor element disposed therein, a solid metal wire also extending inside the flexible tube, and a coil attached to the distal end of the solid wire. The sensor element comprises a pressure sensitive device, e.g. a membrane, with piezoresistive elements connected in a Wheatstone bridge-type of arrangement mounted thereon, examples of which can be found in the present assignee's U.S. Pat. No. 6,343,514. The connection to the external unit is accomplished via a male connector and a corresponding female connector, such that the sensor guide can be disconnected from the external unit, which, for example, allows a catheter to be threaded over the sensor guide and guided into the human or animal body. An example of a suitable external unit is described in U.S. Pat. No. 6,565,514, which is assigned to the present assignee.

For obvious reasons, the outer diameter of a sensor guide has to be relatively small; and so is, for example, the outer diameter of a sensor and guide wire assembly sold and manufactured by the present assignee under the registered trademark PressureWire® only 0.36 mm (0.014 inches) in diameter. As is well-known in the art, the solid metal wire, which can be made from stainless steel or Nitinol® and which also is called the core wire, provides the sensor guide with the necessary stiffness and torqueability. The core wire must therefore have a relatively large diameter, i.e. the core wire occupies a major portion of the available space inside the flexible tube, thereby leaving a very limited space for the signal transmitting cables. Consequently, the signal transmitting cables are very thin, and constitute delicate and sensitive parts of the sensor and guide wire assembly.

The fact that the use of such thin signal transmitting cables poses a potential problem is recognized already in the present applicant's U.S. Pat. No. 6,616,067, wherein it is pointed out that the assembly of a sensor and guide wire assembly to a large extent is a tedious and labour-intensive manual procedure which furthermore has to be executed under a microscope. Further, although different measures can be taken to protect the thin cables from being damaged, they are still sensitive parts of the sensor guide. To solve this problem, the U.S. Pat. No. 6,616,067 discloses a sensor system comprising a first electrode adapted to be in electrical contact with body tissue at a first part of a patient's body and a second electrode adapted to be in electrical contact with body tissue at a second part of the patient's body, such that the sensor system can transfer an electrical signal representing a physiological characteristic through said first and second electrodes via the body tissue. This invention utilizes the core wire to electrically connect the sensor, and the use of thin signal transmitting cables has been eliminated. However, this solution requires that electrical current flows through the patient's body, something which requires that extensive protective measures are taken to eliminate the risk that the current strength becomes too high. As the patient usually is subjected to other medical procedures, and may also be connected to other medical apparatuses, it may further be difficult to find a suitable contact site available for the connection of the second electrode.

Therefore, there remains a need for an improved way of communicating with a guide wire mounted sensor. The sensor should also be inexpensive and easy to manufacture and assemble.

SUMMARY OF THE INVENTION

An object of the present invention is to provide an improved way of communicating with a sensor mounted at the distal end of a guide wire.

Another object is to eliminate the need for the several thin and sensitive signal transmitting cables. A sensor and guide wire assembly according to the present invention should therefore be easy to assembly.

These objects are attained by a sensor assembly arranged to be disposed in a body for measuring a physiological variable, in accordance with claim 1.

According to an aspect of the present invention, there is provided a sensor assembly comprising a sensor element for measuring the physiological variable and to provide a signal representing the measured physiological variable, and a first inductive element arranged to receive energy by means of inductive coupling with a second inductive element that is coupled to an energy supplying means, which second inductive element and energy supplying means are located outside the body, in order to form a power supply for the sensor element.

As used herein, the term "communication" as well as similar terms of that effect are meant to encompass both the transfer of signals from the sensor to an external unit as well as the transfer of energy in the form of an excitation signal from an external unit to the sensor. When there is a need to distinguish between the two types of communications, the former will be referred to as "signal transfer", while the latter is referred to as "feeding", "energizing" or "powering". From the context, it should, however, be easy enough to understand what is meant.

The above objects are achieved by means of a sensor and guide wire assembly of the present invention, which communicates with an external unit by an inductive coupling between a first coil provided in the sensor assembly and a second, external coil which is disposed in or connected to the external unit. The external unit is preferably the same unit that is used to numerically or graphically display the physiological variables that are measured with the sensor and guide wire assembly. With the terminology introduced above, it should here be clear that both the signal transfer from the sensor as well as the energy feeding from the external unit to the sensor may be accomplished through the inductive coupling between the first and second coils. According to the invention, three different ways of arranging the first, internal coil will be presented.

In another basic embodiment of the present invention, the sensor is fed by an inductive coupling between a first coil provided in the sensor assembly and a second, external coil being arranged in or connected to an external unit, whereas the signal transfer is accomplished by a radio frequency signal, i.e. by a dipole antenna. The dipole antenna can be arranged near a pressure sensitive device, e.g., a membrane, at the distal portion of the sensor and guide wire assembly.

Further features of, and advantages with, the present invention will become apparent when studying the appended claims and the following description. Those skilled in the art realize that different features of the present invention can be combined to create embodiments other than those described in the following.

BRIEF DESCRIPTION OF THE DRAWINGS

Preferred embodiments of the present invention will be described in detail in the following with reference made to accompanying drawings, in which.

DESCRIPTION OF PREFERRED
EMBODIMENTS OF THE INVENTION

Figure 1:
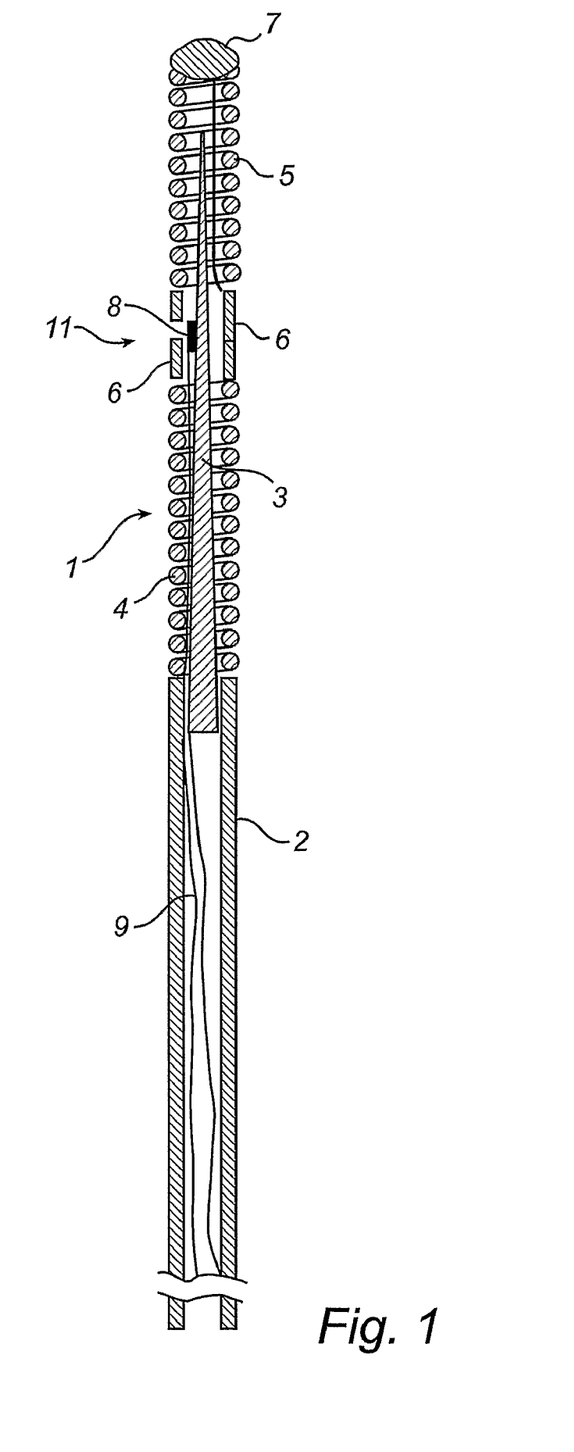
FIG. 1 illustrates schematically the general design of a sensor and guide wire assembly according to prior art.

For better understanding of the context in which a sensor communication arrangement according to the present invention is going to be used, a sensor and guide wire assembly 1 of a conventional design is illustrated in FIG. 1. The sensor guide 1 comprises a hollow tube 2, a core wire 3, a first spiral portion 4, a second spiral portion 5, a jacket or sleeve 6, a dome-shaped tip 7, a sensor element or chip 8, and one or several electrical leads 9. The proximal end of the first spiral portion 4 is attached to the distal end of the hollow tube 2, while the distal end of the first spiral portion 4 is attached to the proximal end of the jacket 6. The proximal end of the second spiral portion 5 is connected to the distal end of the jacket 6, and the dome-shaped tip 7 is attached to the distal end of the second spiral portion 5. The core wire 3 is at least partly disposed inside the hollow tube 2 such that the distal portion of the core wire 3 extends out of the hollow tube 2 and into the second spiral portion 5. The sensor element 8 is mounted on the core wire 3 at the position of the jacket 6, and is through the electrical leads 9 connected to an electronic unit (not shown in the figure). The sensor element 8 comprises a pressure sensitive device in the form of a membrane 10 (not visible in the figure), which through an aperture 11 in the jacket 6 is in contact with a medium, such as blood, surrounding the distal portion of the sensor guide 1.

Figure 2:
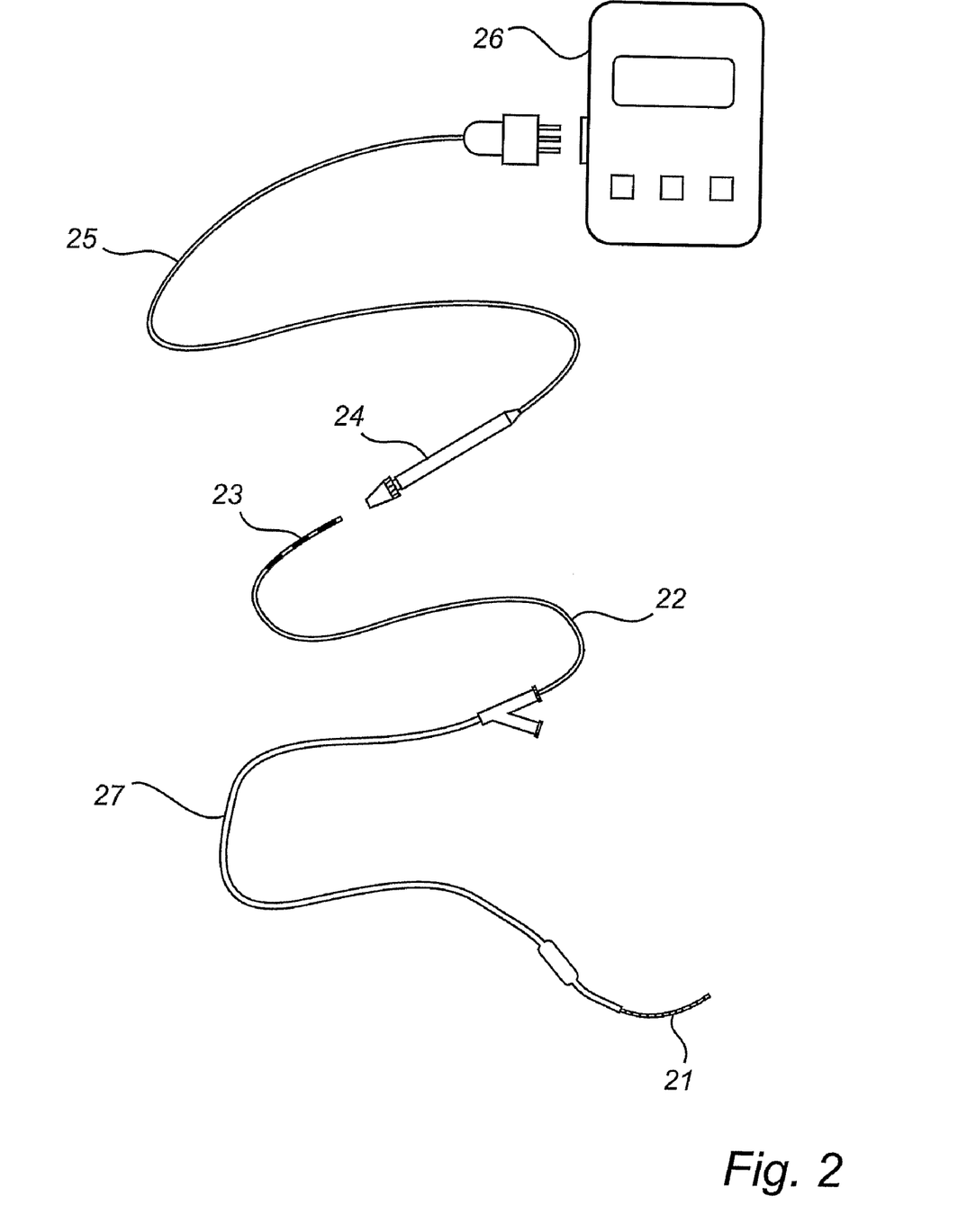
FIG. 2 presents an overview of a sensor measurement system according to prior art.

To further contribute to the understanding of the present invention, an overview of a sensor measurement system of a traditional design is shown in FIG. 2. The sensor measurement system comprises a pressure sensor 21 mounted on a guide wire 22, whose distal end is provided with a male connector 23. A corresponding female connector 24 is provided at one end of an interface cable 25, the other end of which is provided with a plug-in contact for connection to an external unit 26, on which values representing the pressure measured by the pressure sensor 21 can be displayed. Also shown in FIG. 2 is a balloon catheter 27, which has been threaded onto the guide wire 22. This is simply achieved by disconnecting the guide wire 22 from the interface cable 25, and passing the balloon catheter 27 over the guide wire 22; and when the balloon catheter 27 is properly located, the guide wire 22 can again be connected to the interface cable 25 for further measurements. With this known system, the communication between the sensor 21 and the external display unit 26 is accomplished by wire connection; and it should further be clear that this wire connection usually has to be disconnected several times during the medical procedure in which a guide wire mounted sensor is used.

The present invention comprises generally a sensor assembly, which is mounted at a distal portion of a guide wire and is to be positioned inside a living body, and an external unit, such as a monitoring unit, adapted for displaying at least one physiological variable, e.g. pressure or temperature, measured by the sensor part. The external unit is also used to power the sensor assembly and reads signals representing the physiological variable. According to the present invention, the external unit and the sensor assembly communicate with each other without the use of cables that physically and electrically connect the external unit to the sensor assembly, i.e. the communication between the two units is wireless. More particularly, in a first basic implementation of the Present invention, the communication, including both the energizing of the sensor element and other components comprised in the sensor assembly and the signal transfer from the sensor element to the external unit, is solely accomplished through an inductive coupling between the sensor assembly and the external unit. In a second basic implementation, the inductive coupling is merely utilized to feed the sensor with electrical power, whereas the signal transfer is achieved through a radio frequency (RF) signal. Below different embodiments of the present invention are disclosed which show how inductive communication as well as RF signal transfer can be established.

As already indicated above, a sensor assembly arranged at a distal portion of a guide wire can, via an electromagnetic field created by an inductive coupling between a first coil arranged in the sensor assembly and a second coil arranged in an external unit, receive its energy in the form of an excitation signal from the external unit. Hence, the first coil acts as a power supply for the sensor assembly. As was also mentioned, the present invention comprises three different coil arrangements, as will be described in the following. The transfer of a measurement signal from the sensor to the external unit can, on the other hand, for all three coil arrangements be accomplished either through an inductive coupling between the same coils, or through a radio frequency (RF) signal, which is sent by a separate antenna provided at the sensor assembly. This gives in total at least six different embodiments of the present invention.

Figure 3:
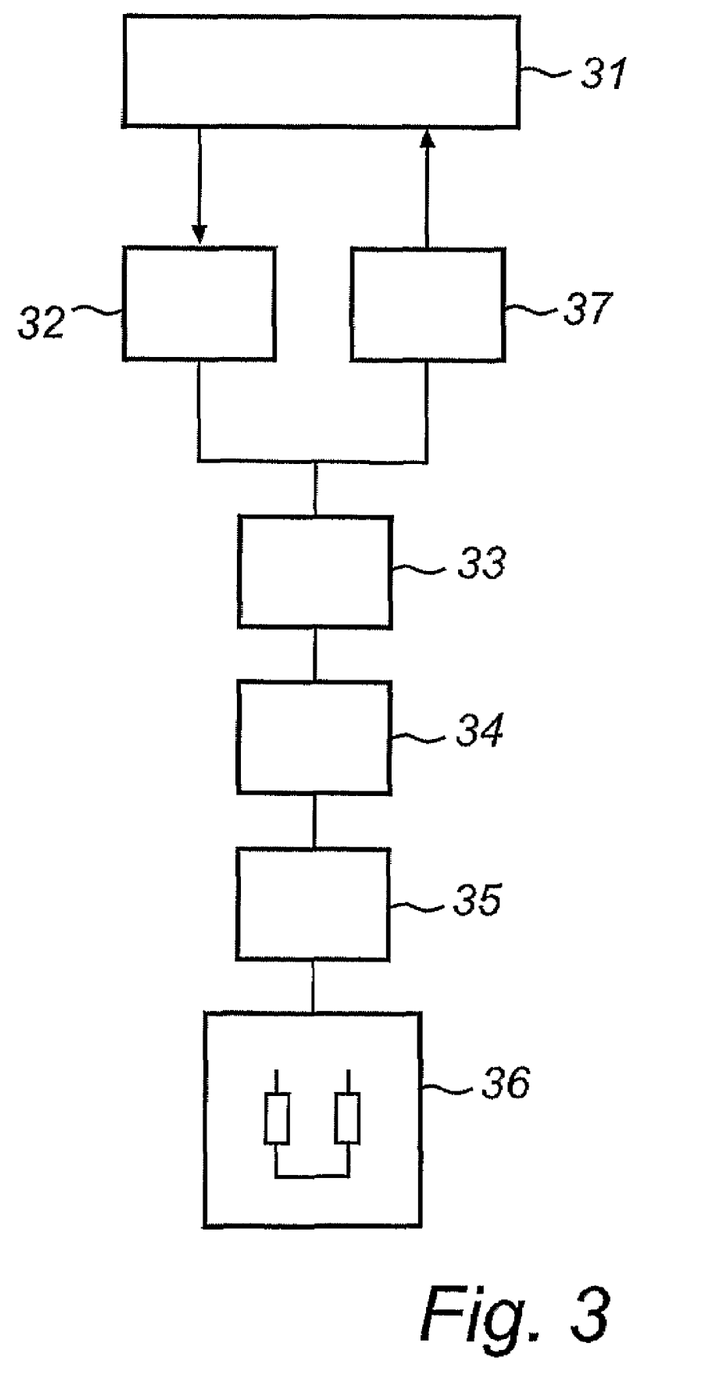
FIG. 3 illustrates the general design of a sensor assembly according to an embodiment of the present invention.

FIG. 3 illustrates the general structure of a sensor assembly according to the present invention. The sensor assembly comprises an interface circuit 31, a power circuit 32, a controller circuit 33, an A/D converter circuit 34, a signal conditioning circuit 35, and a transducer circuit 36 (i.e. a sensor element). In those embodiments that utilize an RF signal for the communication with the sensor, a signal transfer circuit 37 is also included in the sensor assembly. These different units are briefly described below and shown in the accompanying figures. The transducer circuit (or commonly called "the sensor") can be of the type described in the above-referenced U.S. Pat. No. 6,343,514.

Figure 4:
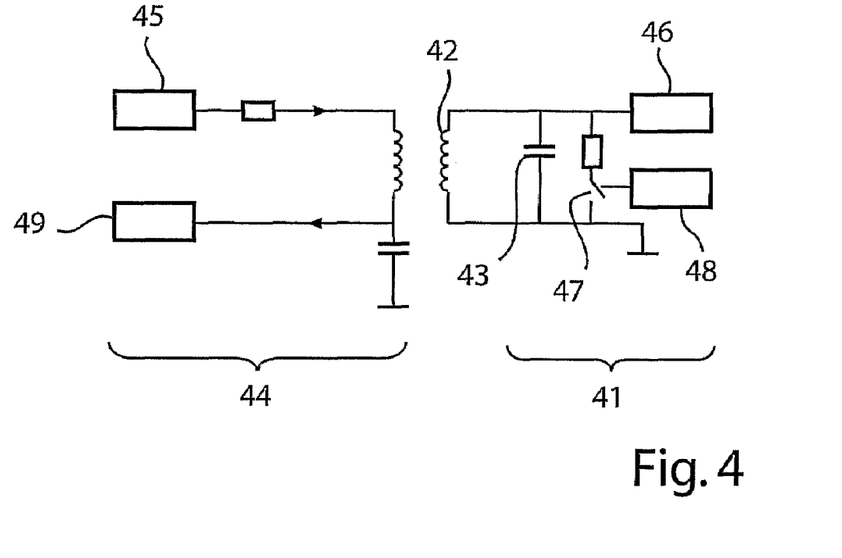
FIG. 4 illustrates schematically a first basic operating principle of the sensor assembly of the present invention.

The first basic operating principle of a sensor assembly according to the present invention is schematically illustrated in FIG. 4. According to this implementation, the powering of the sensor assembly 41 is achieved with magnetic coupled resonant circuits, and a tuned circuit comprising an inductor coil 42 and a capacitor 43 is used as interface circuit. The interface circuit receives energy from reader equipment 44 via an electromagnetic field generated by drive means 45. This received energy is further inductively coupled to the power circuit 46.

As has already been indicated above, signal transfer may also be achieved by communication through the magnetically coupled resonant circuit. Data transfer from the sensor assembly is achieved by modulating 47 the impedance of the interface circuit according to a binary encoded measurement signal originating from the transducer 48. These impedance variations result in variation of the current in the reader equipment, and are further decoded to a digital signal representing the original measurement signal. In FIG. 4, the reader equipment is located outside of the living body. The reader equipment could then be a part of a display unit, such as a monitor 49, or part of a more sophisticated unit also capable of performing manipulations of the data, such as in the above mentioned U.S. Pat. No. 6,565,514.

Figure 5:
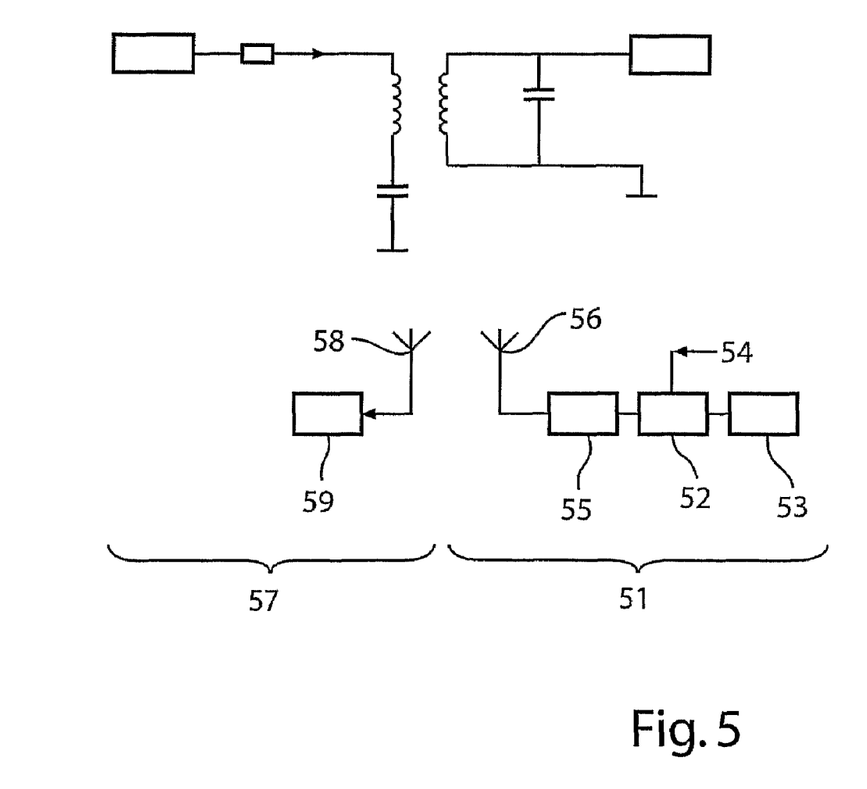
FIG. 5 illustrates schematically a second basic operating principle of the sensor assembly of the present invention.
Figure 6:
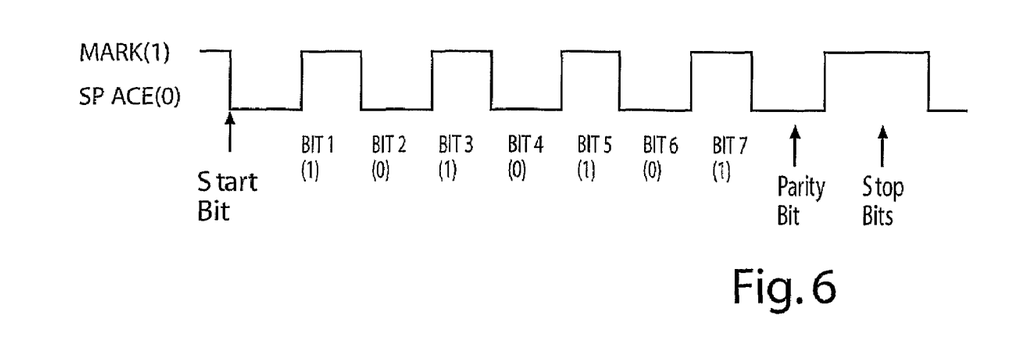
FIG. 6 shows an example of a binary coded digital signal used in communication of a signal representing a measured physiological variable of the present invention.

According to the second basic implementation of the present invention, which is shown in FIG. 5, the signal transfer is instead achieved by a radio frequency (RF) signal. Data transfer from the sensor assembly 51 is realized by modulating 52 an internal oscillator 53 signal according to a binary encoded measurement signal originating from the transducer 54. The resulting radio frequency signal is then fed in to the power amplifier 55 and transmitted by a dipole antenna 56. The reader equipment 57 has a receiver circuit where this radio frequency signal is received via antenna 58 and decoded/demodulated to a digital signal representing the original measurement signal to be displayed on monitoring device 59. The sensor assembly of FIG. 5 is powered similar to that discussed above in conjunction with FIG. 4. An example of a coded digital signal is shown in FIG. 6.

Figure 7:
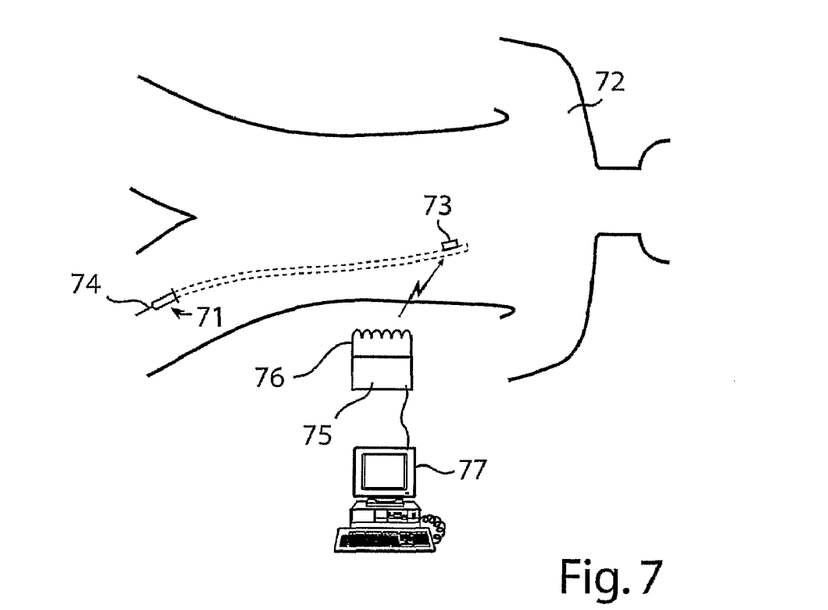
FIG. 7 shows a system for measuring a physiological variable in a body according to an embodiment of the present invention.

The use of a guide wire 71 according to the present invention is schematically shown in FIG. 7. The guide wire is inserted into the femoral artery of a patient 72. The position of the guide wire and sensor assembly 73 inside the body is illustrated with dotted lines. The guide wire 71 is typically provided with a central metal wire (core wire) 74 serving as a support for the sensor assembly. Energy supplying means 75, being part of e.g. a monitoring unit 77, provides an electrical voltage via the air interface to the sensor assembly by means of inductive coupling between coil 76 and a coil (not shown) arranged in the sensor assembly, as has been described in the above.

Figure 8:
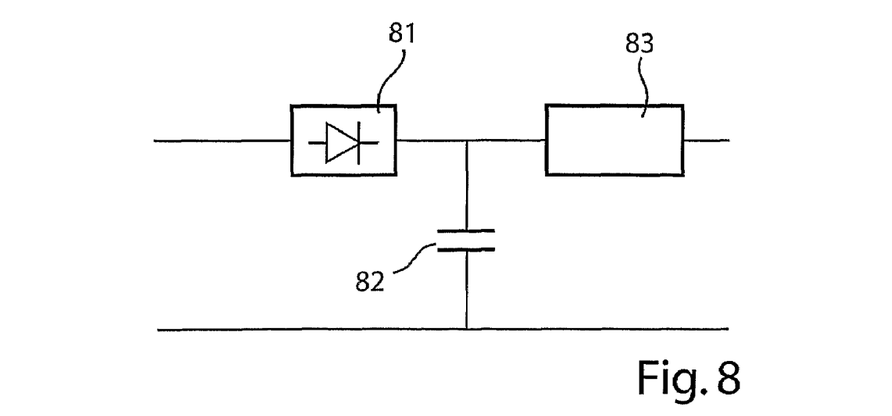
FIG. 8 shows an example of a power circuit used in the present invention.

An example of a power circuit which can be used in the present invention is shown in FIG. 8, and comprises a rectifier 81 and ripple stabilizing capacitor 82 and a voltage regulator 83. Hence, the received signal from the interface-circuit is rectified with the diode rectifier 81. This rectified voltage is stabilized using the capacitor 82 and finally regulated in the voltage regulator 83. This regulated voltage is used for powering different circuits of the sensor assembly.

Figure 9:
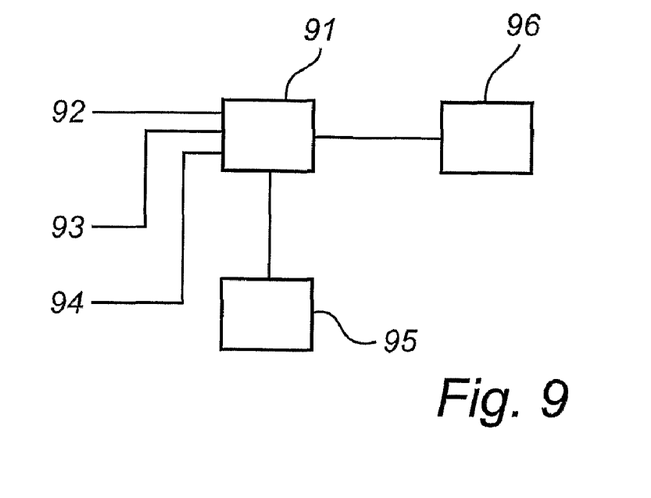
FIG. 9 shows an example of a controller circuit used in the present invention.

FIG. 9 illustrates a controller circuit 91 that can be used in the present invention. The controller is typically equipped with a communication interface 92, an A/D converter interface 93 and general purpose I/O 94. Preferably, the controller also has access to a memory 95 for intermediate or permanent storage of data. The controller circuit receives a digitalized transducer signal from an A/D converter circuit via interface 93. This signal is later encoded in to a binary data stream, optionally with means for error detection and correction. The encoded data stream is then sent to the signal transfer circuit 96.

Figure 10:
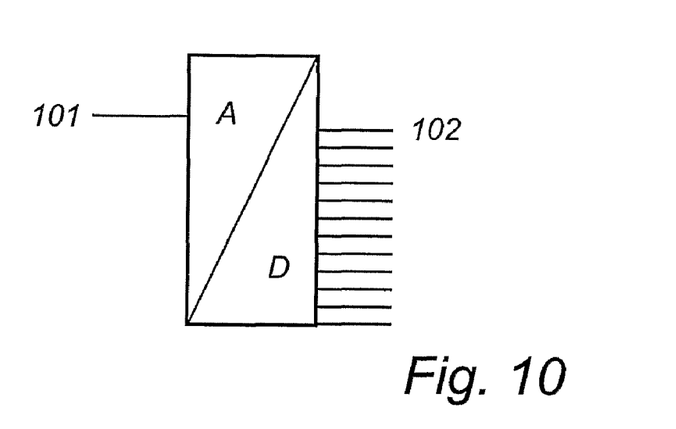
FIG. 10 shows an example of an A/D converter which can be used in the present invention.

An example of an A/D converter is shown in FIG. 10. The A/D converter converts the conditioned analog transducer signal received via signal conditioner interface 101 to digital numerical code to be sent via controller interface 102.

Figure 11:
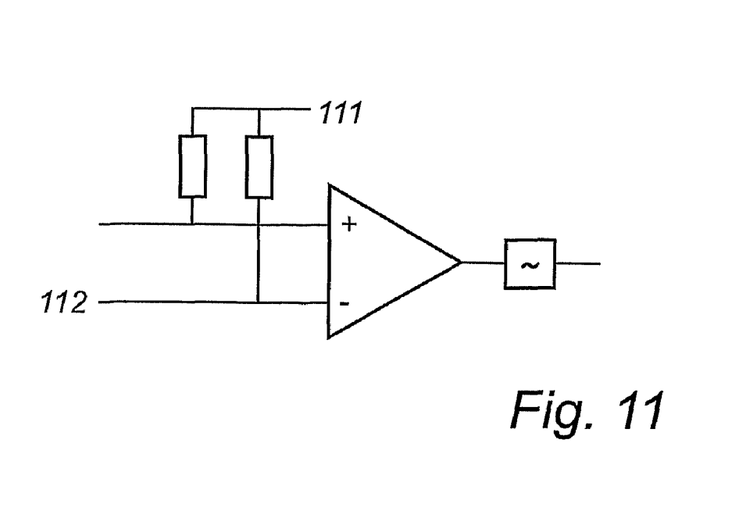
FIG. 11 shows an example of a signal conditioning circuit which can be used in the present invention.

An exemplifying signal conditioning circuit is shown in FIG. 11. The signal conditioning circuit amplifies and filters, by means of an excitation signal 111, signals received from the transducer via interface 112.

A transducer circuit is a circuit that which sensitive to the physiological variable(s) (e.g. pressure, flow, temperature) to be measured. The circuit can comprise a pressure sensitive device, such as a membrane, on which piezoresistive elements are coupled in a Wheatstone-bridge type of arrangement.

In both of the two basic operating principles that have been described above, an internal coil is utilized in the sensor assembly. This internal coil can be arranged in many ways, and below three different embodiments are described.

Figure 12:
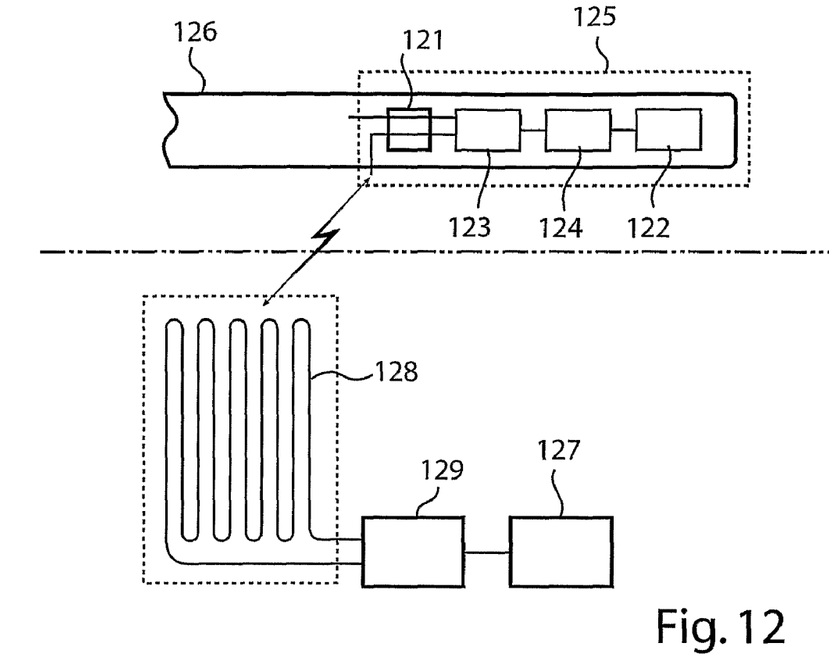
FIG. 12 shows a coil arrangement in accordance with an embodiment of the present invention.

In a first embodiment of the internal coil arrangement, which is illustrated in FIG. 12, a first coil 121 is provided near a sensor element 122, a power and control circuit 123 (possibly comprising a modulator) and a converter circuit 124, which are all part of a sensor assembly 125 arranged in a body at a distal part of guide wire 126. The internal coil arrangement can be provided in the sensor element chip 122 together with a pressure sensitive device, e.g. a membrane, or can be provided as a separate circuit chip 121, which is connected to the sensor chip that comprises the pressure sensitive device. An external unit located outside the body, such as a device 127 for displaying signals representing measured physical variables measured by the sensor element 122 and received from the sensor assembly 125, is inductively coupled to the sensor assembly by means of a second coil 128. A voltage generator 129 generates a voltage across the second coil such that a magnetic field is created between the first and second coil. This magnetic field induces a current in the second coil, which current is employed to drive the sensor assembly 125. Note that in practice, the voltage generator block 129 comprises a receiver for receiving the measured signals from the sensor element 122. As previously discussed, it also comprises a demodulator and possibly some control electronics.

Figure 13:
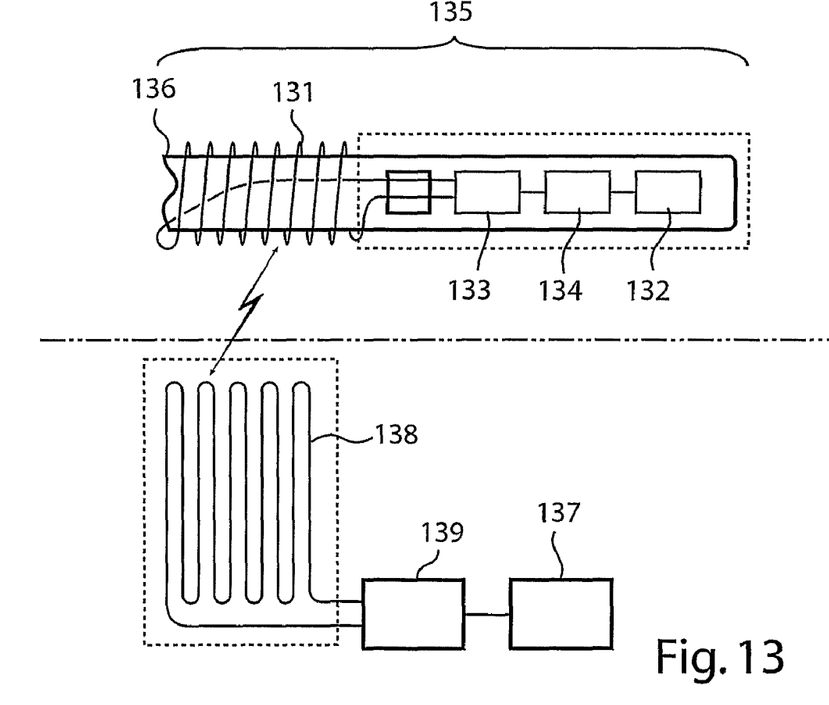
FIG. 13 shows a coil arrangement in accordance with another embodiment of the present invention.

In a second embodiment, which is illustrated in FIG. 13, the first coil is embodied in the form of a first spiral portion 131 wound around the core wire 136 at a distal portion of a guide wire assembly. The metal core wire 136 will then increase the intensity of the magnetic field around the first coil 131 and thereby improve the inductive coupling between the first coil 131 and the second coil 138. In general, as discussed in connection to FIG. 1, this spiral portion is already available in conventional guide wire assemblies for mechanical reasons. Hence, no additional coil is required in the sensor assembly 135. The multiple use of the spiral portion would also contribute to lower production costs. In this second embodiment, in analogy with the first embodiment described in the above, the second external coil 136 is adapted to induce a magnetic field in the first coil 131 and hence act as a power supply for the electronic circuits of the sensor assembly, i.e. the sensor element 132, the power and control circuit 133 (possibly comprising a modulator) and the converter circuit 134. A monitoring device 137 is equipped with an energy generating means 139 to drive the sensor assembly via the inductive coupling of the coils.

Figure 14:
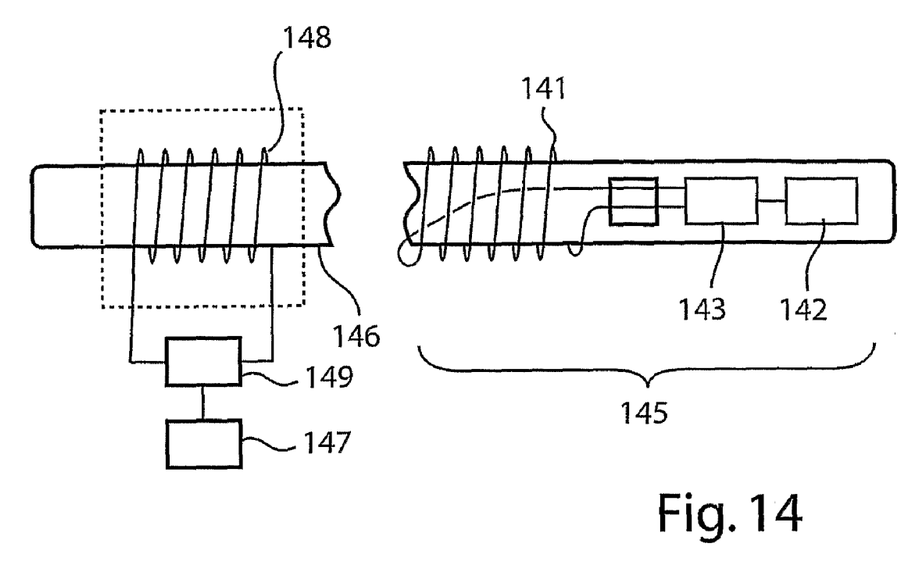
FIG. 14 shows a coil arrangement in accordance with yet another embodiment of the present invention.

FIG. 14 illustrates a third arrangement of an internal coil 141. Here, the first sensor coil is wound around the core wire 146 at a distal portion of a guide wire assembly, as in the second embodiment. As in the previously described embodiments, the sensor assembly 145 is disposed in the body for which physiological variables are to be measured and comprises the first coil 141, the sensor element 142 and a power and control circuit 143 (possibly comprising a modulator). In this third embodiment, a second coil 148 is arranged around the core wire at a proximal portion of the guide wire assembly. To allow other medical devices, such as catheters, to be threaded over and guided by the sensor guide, the second coil is preferably a detachable coil, which is electrically connected to an external unit in the form of a displaying device 147, via an energy generating means 149, by electrical leads.

In the three coil arrangements described in the above, the signals representing measured physical variables measured by the sensor element is communicated to the external device via the inductive coupling of the coils. However, as also has been described, these signals may be communicated by means of dipole antennas.

Even though the invention has been described with reference to specific exemplifying embodiments thereof, many different alterations, modifications and the like will become apparent for those skilled in the art. The described embodiments are therefore not intended to limit the scope of the invention, as defined by the appended claims.

The invention claimed is:

1. A sensor assembly arranged to be disposed in a body for measuring a physiological variable, the sensor assembly comprising:
   a sensor element fixedly mounted at a distal portion of a guide wire for measuring the physiological variable and to provide a signal representing the measured physiological variable; and
   a first coil positioned at the distal portion of the guide wire and arranged to receive energy by inductive coupling with a second coil that is coupled to an energy supply, wherein the second coil and energy supply are adapted to be located outside the body, in order to form a power supply for the sensor element, wherein the second coil is detachably arranged around a core wire at a proximal portion of the guide wire.

2. The sensor assembly in accordance with claim 1, wherein the first coil is a spiral portion available in a guide wire assembly at which the sensor assembly is arranged.

3. The sensor assembly in accordance with claim 1, further being arranged to communicate the signal representing the measured physiological variable via the first coil.

4. The sensor assembly in accordance with claim 1, further comprising:
   an antenna arranged to communicate the signal representing the measured physiological variable.

5. The sensor assembly in accordance with claim 3, further comprising:
   a modulator arranged to modulate a carrier signal with the signal representing the measured physiological variable before the modulated carrier signal is communicated.

6. A system comprising the sensor assembly in accordance with claim 1 and a monitoring device, said monitoring device comprising said energy supply.

7. The system of claim 6, wherein said monitoring device further comprises:
   a demodulator arranged to demodulate the signal representing the measured physiological variable, wherein the monitoring device is further arranged to provide a representation of said measured physiological variable.

8. The sensor assembly in accordance with claim 1, wherein the guide wire has an outer diameter of approximately 0.36 mm.

* * * * *